United States Patent [19]
Hürter et al.

[11] Patent Number: 5,358,515
[45] Date of Patent: Oct. 25, 1994

[54] MICROWAVE HYPERTHERMIA APPLICATOR

[75] Inventors: Willibald Hürter, Heidelberg; Fritz Reinbold, Sandhausen, both of Fed. Rep. of Germany

[73] Assignee: Deutsches Krebsforschungzentrum Stiftung des Offentlichen Rechts, Heidelberg, Fed. Rep. of Germany

[21] Appl. No.: 671,877
[22] PCT Filed: Aug. 16, 1990
[86] PCT No.: PCT/DE90/00627
  § 371 Date: Jun. 17, 1991
  § 102(e) Date: Jun. 17, 1991
[87] PCT Pub. No.: WO91/02560
  PCT Pub. Date: Mar. 7, 1991

[30] Foreign Application Priority Data
Aug. 16, 1989 [DE] Fed. Rep. of Germany ....... 3926934

[51] Int. Cl.$^5$ ................................................ A61N 1/06
[52] U.S. Cl. ................................. 607/101; 607/113; 607/116; 607/156
[58] Field of Search ............... 607/46, 113, 116, 154, 607/101, 156; 600/9–11; 606/27, 32, 33

[56] References Cited

U.S. PATENT DOCUMENTS

| | | |
|---|---|---|
| 2,767,397 | 10/1956 | Byrne . |
| 3,230,957 | 1/1966 | Seifert ................................. 128/804 |
| 4,612,940 | 9/1986 | Kasevich et al. . |
| 4,700,716 | 10/1987 | Kasevich et al. . |
| 4,841,988 | 6/1989 | Fetter et al. ......................... 128/784 |
| 4,865,047 | 9/1989 | Chou et al. .......................... 607/101 |

FOREIGN PATENT DOCUMENTS

3831016  3/1990  Fed. Rep. of Germany .

OTHER PUBLICATIONS

K. Lange et al, "Taschenbuch der Hochfrequenztechnik", Springer-Verlag, 1985, pp. L1–L7 and N1–N14.
O. Zinke et al, "Lehrbuch der Hochfrequenztechnik", Springer-Verlag, 1965, pp. 104–112.
"Electromagnetics" vol. 1, 189 GB; pp. 51–72; King et al.

*Primary Examiner*—Lee S. Cohen
*Assistant Examiner*—Brian L. Casler
*Attorney, Agent, or Firm*—Spencer, Frank & Schneider

[57] ABSTRACT

The antenna system of the invention is insulated on the outside and when inserted in a dissipative medium has a fixed complex resistance. When the antenna is supplied with HF energy through a coaxial cable, only that area of the medium immediately around the antenna is heated. The area surrounding the insulated HF feed line is not heated, or such heating is negligible, since, owing to the fixed complex resistance of the antenna in the medium, any return of energy along the feed line is prevented. The antenna system of the invention is suitable for use in the tumor-therapy field as a hyperthermic microwave applicator for limited local heating of cancerous tissue.

13 Claims, 4 Drawing Sheets

MICROWAVE HYPERTHERMIA APPLICATOR

BACKGROUND OF THE INVENTION

The invention relates to a microwave hyperthermia applicator for heating a limited environment in a dissipative medium, particularly for heating diseased tissue in the human body.

Hyperthermia as brain tumor therapy places special requirements on the treatment system. High blood flow, particular temperature sensitivity of the healthy brain tissue and the limited possibility for surgical treatment of the tumor necessitate a hyperthermia system which is particularly compact and permits sufficiently high thermal energy deposition in a predetermined and limited region in the brain.

German patent application P 3,831,016.3 (and the corresponding German published patent application DE 3,831,016 A1, published Mar. 15, 1990), discloses microwave hyperthermia applicators, antenna arrangements for locally heating a dissipative medium, the tumor-afflicted human tissue. In this case, the incorporation of line transformers at the end of a coaxial feeder cable for a dipole antenna makes it possible for heating to take place only around the dipole antenna, namely in the diseased human tissue and less along the outer sheath of the feeder cable, namely in the healthy human tissue.

Microwave hyperthermia applicators as disclosed in German Patent Application DE 3,831,016.3 still conduct a considerable portion of electrical energy back over the outer conductor so that the dissipative medium is heated.

Another patent, U.S. Pat. No. 4,700,716, discloses and claims a coaxial applicator arrangement which is excited at a proximal end that is not utilized to heat the environment and is there also provided with a termination including a $\lambda/4$ sleeve. The thinner region of the subsequent, distal end of the coaxial applicator arrangement then serves to actually heat the environment if the latter is composed of a heatable medium. This applicator is no dipole antenna. Due to the radiation characteristic, it is not possible to heat a narrowly defined region by electromagnetic radiation as precisely as with the dipole antenna arrangement according to the invention.

SUMMARY OF THE INVENTION

It is the object of the invention to improve the structure of the dipole and monodipole applicators disclosed in the above mentioned German Patent Application P 3,831,016.3 so that heating of the dissipative medium remains limited to the region around the antenna.

The object is accomplished according to a first embodiment of the invention by a microwave hyperthermia applicator, having a defined limited distribution of the electromagnetic field, in the form of a dipole antenna which, on the outer sheath of the coaxial feeder cable for the antenna, is provided with a covering to change the impedance, and wherein: the covering below and adjacent the dipole half connected with the outer sheath of the feeder cable, is filled with a predetermined dielectric medium and is a $\pi/2$ or a $\pi$ transformer; and the outwardly insulated system composed of the dipole antenna, transformer, and the coaxial feeder cable, forms a defined complex resistance with the dissipative medium that primarily surrounds the dipole antenna so that heating of the dissipative medium is limited directly to a predeterminable area around the dipole, and thus there is no heating of the dissipative medium along the outer sheath of the feeder cable.

The above object is achieved according to a further embodiment of the invention wherein the antenna is a monopole antenna and wherein the covering filled with a dielectric medium is a $\pi/2$ transformer which is disposed at the same location as the dipole half connected with the coaxial outer sheath of the dipole embodiment, so that the outwardly insulated system, composed of the monopole antenna, the $\pi/2$ transformer and the coaxial feeder cable, forms a defined complex resistance with the dissipative medium surrounding primarily the monopole antenna so that heating of the dissipative medium is limited directly to a predeterminable area surrounding the monopole, and thus there is no heating of the dissipative medium along the outer sheath of the feeder cable.

The remaining dependent claims disclose an advantageous incorporation of the line transformer ahead of the antenna at the end of the coaxial feeder cable.

The advantages realized with the invention are that indeed only the dissipative medium surrounding the antenna is heated, namely in that now a defined complex resistance is present at the end of the cable and thus no, or no significant, energy feedback occurs any longer through the outer sheath of the feeder cable.

Two embodiments, namely the microwave hyperthermia applicator as a dipole antenna and as a monopole antenna, are illustrated in the drawing figures and will be described in greater detail below.

DETAILED DESCRIPTION OF THE PREFERRED EMBODIMENTS

Figure 1:
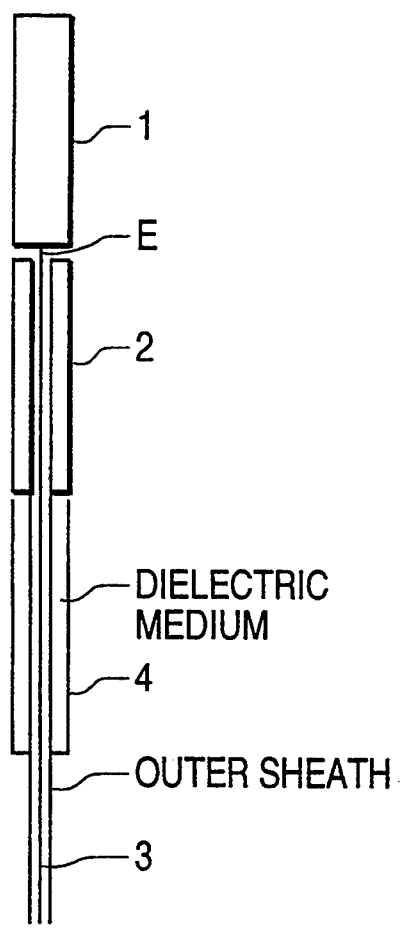
FIG. 1 is a schematic illustration of a dipole antenna including a $\pi/2$ (or $\pi/4$) transformer according to the invention.

FIG. 1 shows the microwave hyperthermia applicator as a dipole including an upper dipole half 1 and a lower dipole half 2. As is known, with this type applicator, the upper dipole half 1 is a widened metal extension of the inner conductor of a coaxial feeder line or cable 3, while the lower dipole half 2 is a metal cylinder connected to the outer sheath of the coaxial feeder cable 3, with both of these dipole elements or halves 1 and 2 being of the same diameter, as schematically shown in FIG. 1. The applicator of FIG. 1 differs from that disclosed in Patent Application DE 3,831,016.3 in that the $\pi/2$ ($\lambda/4$) transformer 4 is separated from the lower dipole half 2 that is connected with the outer sheath of the coaxial feeder cable 3. At the upper end as well as at the lower end of the dipole, which is fed from the center E, the current is zero. The $\pi/2$ transformer 4, which generally comprises a metal outer cylindrical sheath of the correct length, e.g., a portion of the outer conductor of a triaxial cable, is filled with a dielectric medium.

Figure 2:
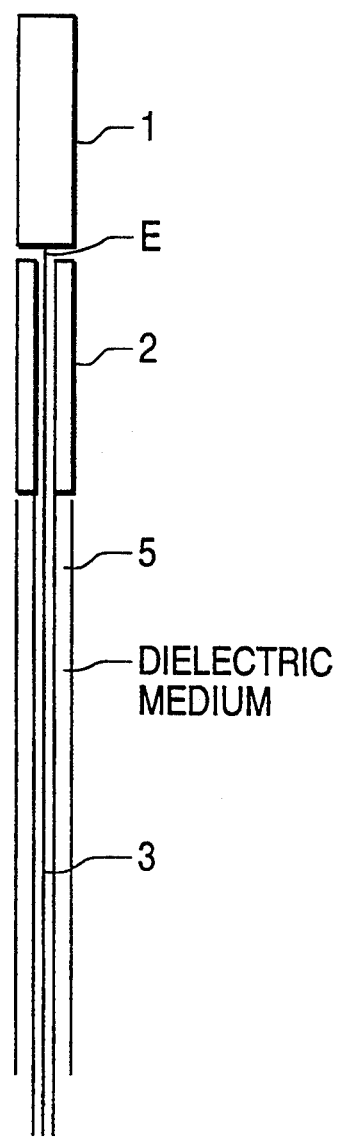
FIG. 2 is a schematic illustration of a dipole antenna including a (or $\pi/2$) transformer transformers according to the invention.

In the illustrated embodiment, the end of the $\pi/2$ transformer 4 facing and adjacent the lower dipole half 2 is open and spaced from the dipole half 2, while the end of the $\pi/2$ transformer remote from the dipole half 2, i.e. the end facing the HF generator (not shown) connected to the cable 3, is closed, i.e. connected to the outer sheath of the cable 3, as shown. With a given total length and constant parameters for the insulating dielectric medium and the surrounding dissipative medium, the complex resistance of this antenna is constant. A feedback of energy through the outer sheath of the feeder cable 3 to the HF generator and thus heating of the healthy tissue surrounding the feeder cable 3 is not possible. FIG. 2 shows the dipole antenna according to FIG. 1 but including a $\pi$ ($\pi/2$) transformer 5 which is formed generally in a manner similar to that of the $\pi/2$ transistor 4. However, in this embodiment an open line end is produced at both ends. The mechanical structure is even simpler than for the dipole antenna according to FIG. 1.

Figure 3:
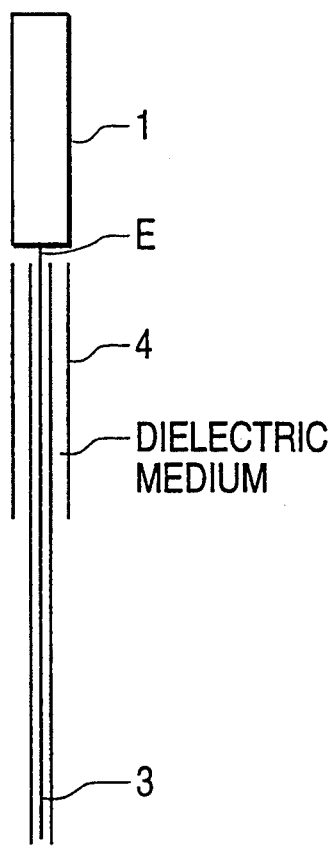
FIG. 3 is a schematic illustration of a monopole antenna including an open $\pi/2$ transformer according to the invention.

FIG. 3 is a schematic representation of a microwave hyperthermia applicator configured as a monopole antenna. An open line end is produced by the $\pi/2$ transformer 4 which ends at antenna feed point E. This transformer 4 produces a short-circuit at the location of the conductive surface (see, in this connection, the above mentioned German Patent Application P 3,831,016.3).

Figure 4:
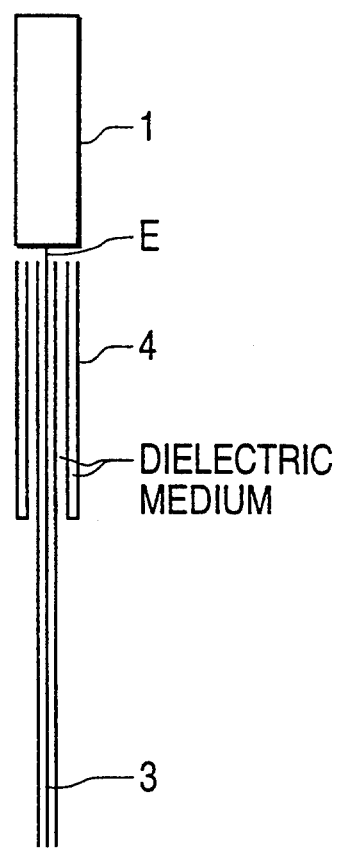
FIG. 4 is a schematic illustration of a monopole antenna including two concentric $\pi/2$.

In order to be able to realize an even greater concentration of the energy output, several $\pi/2$ transformers 4 are arranged, as shown in FIG. 4, coaxially around the feeder cable 3 seen from the input location E in the direction of the generator.

These transformers suppress residual currents feeding back to the HF generator. In this arrangement the internal $\pi/2$ transformer produces an open line end and the external $\pi/2$ transformer produces a short-circuited line end.

Figure 5:
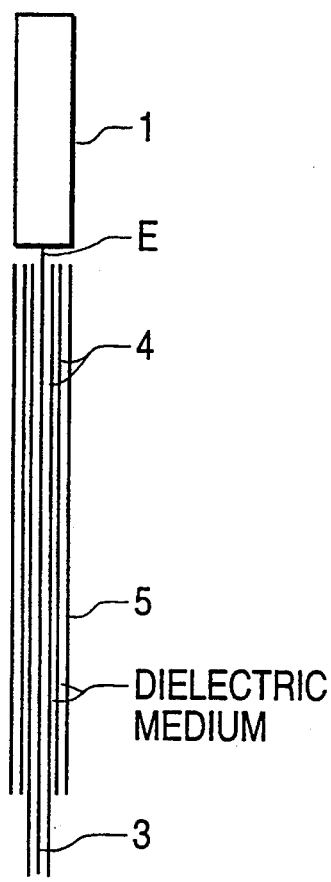
FIG. 5 is a schematic illustration of a monopole antenna including an outer $\pi$ transformer and two inner $\pi/2$ transformers, which all are open at both ends, respectively, according to the invention.

An embodiment of the microwave hyperthermia applicator comparable to FIG. 4 is the monopole antenna of FIG. 5. The transformers 4 and 5 produce open line ends in the interior (the two $\pi/2$ transformers 4) and on the exterior (the $\pi$ transformer 5).

Figure 6:
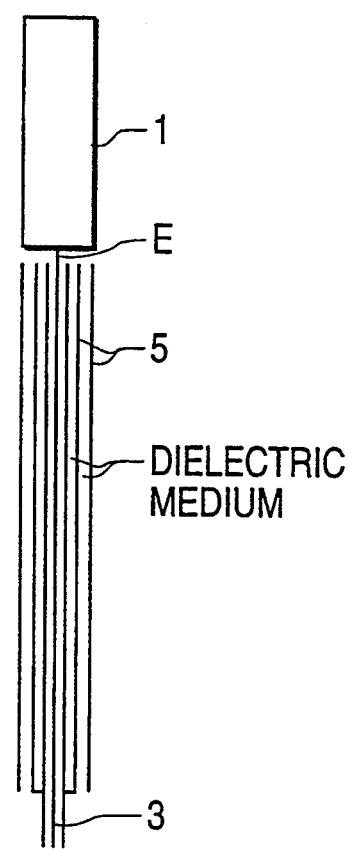
FIG. 6 is a schematic illustration of a monopole antenna including an inner $\pi$ (or $\pi/2$) transformer and an outer $\pi$ (or $\lambda/2$) transformer according to the invention.

FIG. 6 shows the microwave hyperthermia applicator as a monopole including an internal $\pi$ transformer 5 which is closed in the direction of the generator, i.e., at its lower end in the figure. The closed $\pi$ transformer 5 is in turn surrounded by a further $\pi$ transformer 5 that is open on both sides or ends as shown.

The applicators according to the invention show that the energy output is highly concentrated around the feed point E up to the antenna tip (monopole) or antenna tips (dipole). Along the coaxial feeder line 3 up to feed point E, there is no, or only negligibly little, heating of the environment. In the practical case this means protection of the healthy human tissue.

Figure 7:
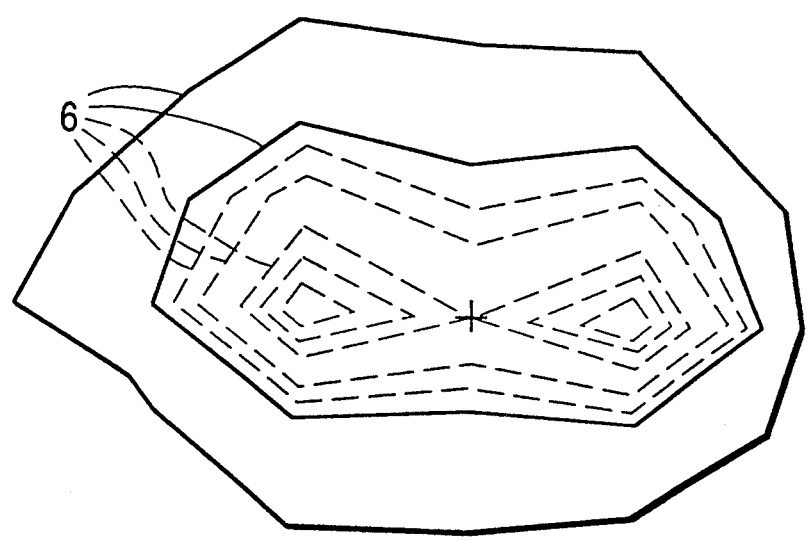
FIG. 7 shows a hyperthermia diagram for a dipole antenna as the applicator.

Field intensity measurements around the dipole antenna according to the invention, which had been immersed into a dissipative medium for this purpose, are shown in FIG. 7. The composition of the medium is stated in the above mentioned German Patent Application P 3,831,016.3. The complex permittivity corresponds to that of brain tissue. The lines in FIG. 7 describe iso-SAR (specific absorption rate) contours. They are presented as 10% steps. The SAR is a measure for the power received per mass of dissipative medium. It is proportional to the square of the amount of electrical field intensity. The energy is fed in at point E of a dipole antenna according to the invention. The feeder line to the antenna goes from the left of the generator to E, to the feed point of the antenna, parallel to the abscissa.

The closed SAR lines 6 indicate the local heating of the dissipative medium around the antenna, with the heating remaining essentially limited to that area.

We claim:

1. In a microwave hyperthermia applicator having a defined limited distribution of its electromagnetic field comprising an outwardly insulated system including a dipole antenna having a first dipole half which is an extension of a center conductor of a coaxial feeder cable for the antenna and a second dipole half adjacent said first dipole half and extending along and being connected to an outer sheath of said coaxial feeder cable; the improvement wherein:

a conductive covering surrounds a portion of the outer sheath of the feeder cable to change an impedance of the applicator;

said covering has an open first end adjacent but spaced from the second dipole half, is filled with a dielectric medium and forms one of a $\pi/2$ and a $\pi$ transformer; and, the outwardly insulated system composed of the dipole antenna, the transformer and the coaxial feeder cable forms a defined complex resistance with a dissipative medium that primarily surrounds the dipole antenna during use so that heating of the dissipative medium is limited directly to a predeterminable area around the dipole and thus there is no heating of the dissipative medium along the outer sheath of the feeder cable.

2. An applicator according to claim 1 wherein said covering is coaxial with the coaxial feeder cable and forms a $\pi/2$ transformer.

3. A microwave hyperthermia applicator according to claim 2, wherein said covering has a second end opposite said first end, with said second end being electrically connected with said outer sheath of said feeder cable.

4. An applicator according to claim 1 wherein said covering is coaxial with the feeder cable and forms a $\pi$ transformer.

5. A microwave hypothermia applicator according to claim 4, wherein said covering has a second end opposite said first end, with both of said first and second ends being open.

6. In a microwave hyperthermia applicator having a defined limited distribution of its electromagnetic field comprising an outwardly insulated system including a monopole antenna which is an extension of a center conductor of a coaxial feeder cable for the antenna; the improvement wherein:

a conductive covering surrounds a portion of an outer sheath of the feeder cable to change an impedance of the applicator;

said covering has a first open end adjacent but spaced from the monopole antenna, is filled with a dielectric medium and forms at least one of a $\pi/2$ and a $\pi$ transformer; and, the outwardly insulated system composed of the monopole antenna, the transformer and the coaxial feeder cable forms a defined complex resistance with a dissipative medium that primarily surrounds the monopole antenna during use so that heating of the dissipative medium is limited directly to a predeterminable area around the monopole, and thus there is no heating of the dissipative medium along the outer sheath of the feeder cable.

7. An applicator according to claim 6 wherein said covering is coaxial with the coaxial feeder cable and forms a first $\pi/2$ transformer which is open at both ends.

8. An applicator according to claim 7 wherein: a further conductive covering filled with a dielectric medium and forming a second $\pi/2$ transformer is disposed coaxial with said first $\pi/2$ transformer, with the conductive coverings of the two transformers being connected with one another only at their respective ends facing away from the antenna.

9. An applicator according to claim 7 wherein: said conductive covering is open at both ends; a further conductive covering, which is open at both ends, which is filled with a dielectric medium and which forms a second $\pi/2$ transformer, is disposed coaxially with the feeder cable and adjacent said first $\pi/2$ transformer; and another conductive covering, which is open at both ends, which is filled with a dielectric medium and which forms a $\pi$ transformer, is disposed around and coaxially with said first and second $\pi/2$ transformers.

10. An applicator according to claim 6 wherein: said conductive covering forms a first $\pi$ transformer whose end facing away from said antenna is connected to said outer sheath of said coaxial cable; and a further conductive covering coaxially surrounds said first $\pi$ transformer, is filled with a dielectric medium and forms a $\pi$ transformer which is open at both ends.

11. In a microwave hyperthermia applicator having a defined limited distribution of its electromagnetic field comprising: a dipole antenna having a firs dipole element which is an extension of a center conductor of a coaxial feeder cable for the antenna and a second dipole element, of the same diameter as said first dipole element, disposed adjacent said first dipole element and extending along and being connected to an outer sheath of said coaxial feeder cable; and means disposed on said outer sheath of said coaxial feeder cable for changing the impedance of the applicator; the improvement wherein said means is one of a $\pi/2$ and a $\pi$ transformer formed of a conductive cylindrical sheath which surrounds a portion of and is coaxial with said coaxial cable, which has a first open end adjacent but spaced from said second dipole element, which is filled with a dielectric medium, and which has the same diameter as said dipole elements.

12. A microwave applicator according to claim 11, wherein said means is a $\pi/2$ transformer and a second end of said cylindrical conductive sheath is connected to said outer sheath of said coaxial feeder cable.

13. A microwave applicator according to claim 11, wherein said means is a $\pi$ transformer and said cylindrical conductive sheath is open at both of its ends.

* * * * *